(12) United States Patent
Kobayashi (10) Patent No.: US 7,108,699 B2
(45) Date of Patent: Sep. 19, 2006

(54) CLIP DEVICE FOR HOLDING A LIVING TISSUE

(75) Inventor: Tsukasa Kobayashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/760,058

(22) Filed: Jan. 16, 2004

(65) Prior Publication Data

US 2004/0147943 A1 Jul. 29, 2004

(30) Foreign Application Priority Data

Jan. 17, 2003 (JP) ............................ 2003-010154

(51) Int. Cl.
  *A61B 17/10* (2006.01)
(52) U.S. Cl. ........................ 606/142; 606/151; 606/157
(58) Field of Classification Search ........ 606/139–158, 606/205–211
  See application file for complete search history.

(56) References Cited

U.S. PATENT DOCUMENTS

| 4,038,987 | A | * | 8/1977 | Komiya ...................... 606/142 |
| 4,929,240 | A | * | 5/1990 | Kirsch et al. ................ 606/151 |
| 5,049,153 | A | * | 9/1991 | Nakao et al. ................ 606/151 |
| 6,648,898 | B1 | * | 11/2003 | Baxter ......................... 606/142 |
| 2002/0045909 | A1 | * | 4/2002 | Kimura et al. .............. 606/151 |
| 2002/0151916 | A1 | | 10/2002 | Muramatsu et al. |
| 2002/0173805 | A1 | | 11/2002 | Matsuno et al. |

FOREIGN PATENT DOCUMENTS

| EP | 0 738 501 A1 * | 10/1996 | .................. 606/142 |
| JP | 4-102450 | 4/1992 | |

* cited by examiner

*Primary Examiner*—Glenn K. Dawson
(74) *Attorney, Agent, or Firm*—Scully, Scott, Murphy & Presser, P.C.

(57) ABSTRACT

A clip device for holding a living tissue, wherein a clip operating force adjustment portion is provided with a hold member placed in a state of relatively increasing a ratio of a clip closing force to close clip hands to a clip opening force to expand the clip hands of a clip when operating the clip.

18 Claims, 6 Drawing Sheets

CLIP DEVICE FOR HOLDING A LIVING TISSUE

CROSS-REFERENCE TO RELATED APPLICATIONS

This application is based upon and claims the benefit of priority from the prior Japanese Patent Application No. 2003-10154, filed Jan. 17, 2003, the entire contents of which are incorporated herein by reference.

BACKGROUND OF THE INVENTION

1. Field of the Invention

The present invention relates to a clip device for holding a living tissue, which is inserted into a living body through an endoscope channel, and used to stop bleeding and to mark a part to be medically treated.

2. Description of the Related Art

A known clip device is generally inserted into a living body through an endoscope channel, and left in a cavity of a living body in the state clipping a living tissue, for example, a mucus membrane in the cavity and a blood vessel.

Figures 8A, 8B, 8C:
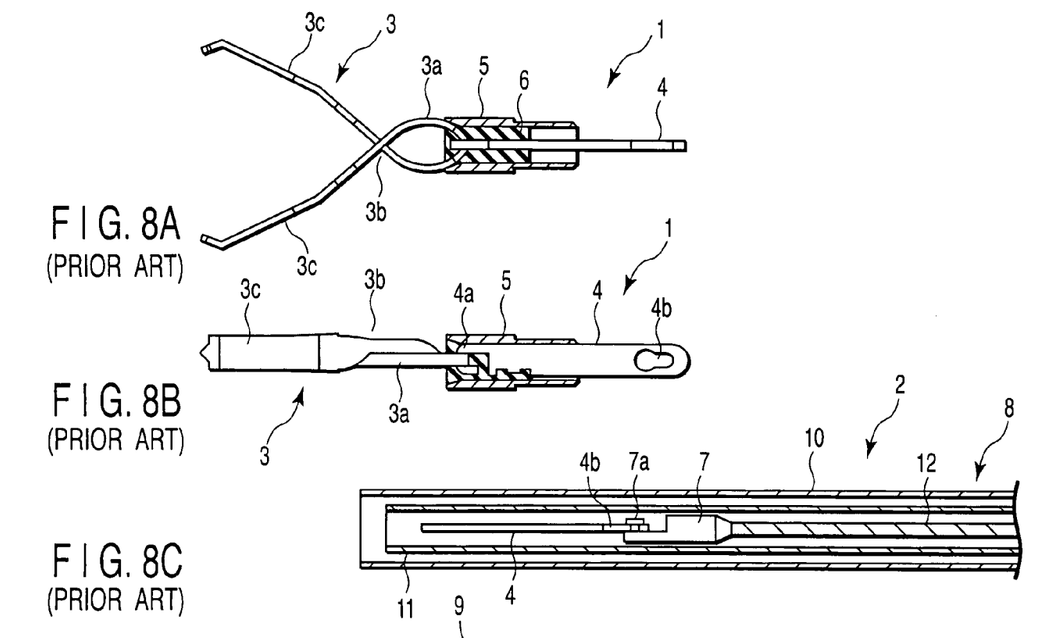
FIG. 8A is a longitudinal sectional view showing a clip unit of a conventional living tissue apparatus.
FIG. 8B is a longitudinal sectional view of a clip unit showing the clip of FIG. 8A seen from the side.
FIG. 8C is a side view showing a connected part of a connection plate and a control wire.

This type of clip device is disclosed by Jpn. Pat, Appln. KOKAI Publication No. 4-102450 (patent document 1), for example. This application discloses a device which comprising a clip unit 1 shown in FIGS. 8A and 8B, and a clip control unit 2 shown in FIGS. 8C and 8D. The clip unit 1 is provided with a α-shaped clip 3, as shown in FIG. 8A. The clip 3 is made of thin metal plate (a part of clip) bent at the center, forming a substantially ring-like base ring 3a. Further, a pair of clip hands 3c extends almost straight from the base ring 3a, crossing each other at a point 3b. The clip 3 has the characteristic of expanding in the direction of separating the clip hands 3c.

Further, this clip device has a plate-like connection member 4, a holder tube 5 for tightening a clip, and a hold member 6. The connection member 4 is engaged with the base ring 3a of the clip 3. The holder tube 5 is fit around the connection member 4, and has a diameter smaller than the base ring 3a. The hold member 6 is filled in the holder tube 5, and holds the connected part of the base ring 3a and connection member 4.

A substantially J-shaped hook (an engagement part) 4a is provided at the front end of the connection member 4, as shown in FIG. 8B. The hook 4a is engaged with the base ring 3a. The hold member 6 is made of filler such as silicone. An engagement hole 4b is provided in the base end of the connection member 4. The engagement hole 4b is engaged with a connection pin 7a of a hook unit 7 of the clip control unit 2 described later.

The grip control unit 2 consists of a slender insertion part 8 and a control unit 9 for connecting the close-to-hand side of the insertion part 8. The insertion part 8 has a lead-in tube 10, a control tube 11, and a control wire 12, as shown in FIG. 8C. The control tube 11 is inserted into the lead-in tube 10. The control wire 12 is inserted into the control tube 11. The hook unit 7 is provided at the front end of the control wire 12. The hook unit 7 has the pin 7a for connecting the connection member 4.

Figure 8D:
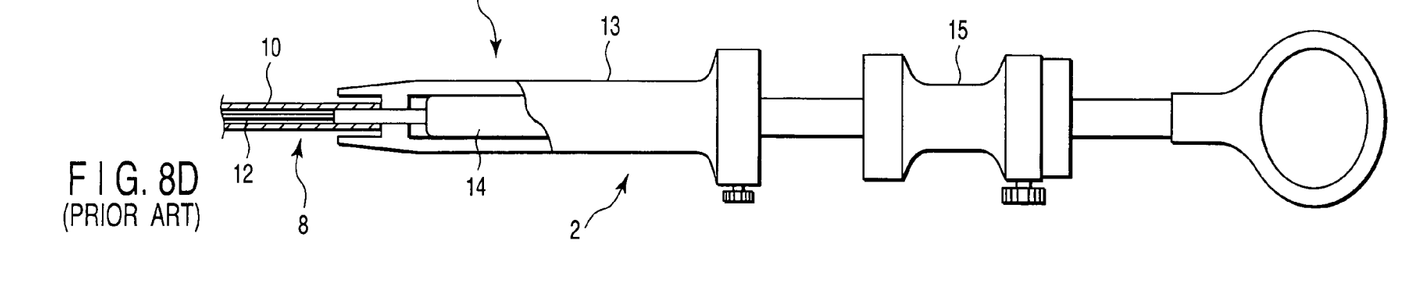
FIG. 8D is a side view of a control unit close to hand for pulling a control wire.

As shown in FIG. 8D, the control unit 9 has a tube coupler 13, a main control unit 14, and a slider unit 15. The tube coupler 13 is fixed to the close-to-hand side of the lead-in tube 10. The main control unit 14 moves the control tube 11 forward and rearward. The slider unit 15 moves the control wire 12 forward and rearward.

The clip unit 1 is fixed to the control unit 2, and led into a living body cavity, in the following six steps.

(1) Push the main control unit 14 of the clip control unit 2 toward the front end side, and project the control tube 11 from the lead-in tube 10.

(2) Push the slider unit 15 toward the front end side, and project the hook unit 7 from the control tube 11.

(3) Adjust the positions of the engagement hole 4b of the connection member 4 of the clip unit 1 and the pin 7a of the hook unit 7 of the clip control unit 2, and insert and engage the pin 7a into the engagement hole 4b.

(4) Pull the slider unit 15 toward the base end side, and fit the holder tube 5 to the front end of the control tube 11.

(5) Pull the main control unit 14 toward the base end side, and house the clip unit 1 into the lead-in tube 10.

(6) Insert the insertion part 8 of the clip control unit 2 into a living body cavity through an endoscope channel.

Next, close the clip unit 1 in the following steps.

(1) Push the main control unit toward the front end side, and project the clip unit 1 from the lead-in tube 10.

Figure 9A:
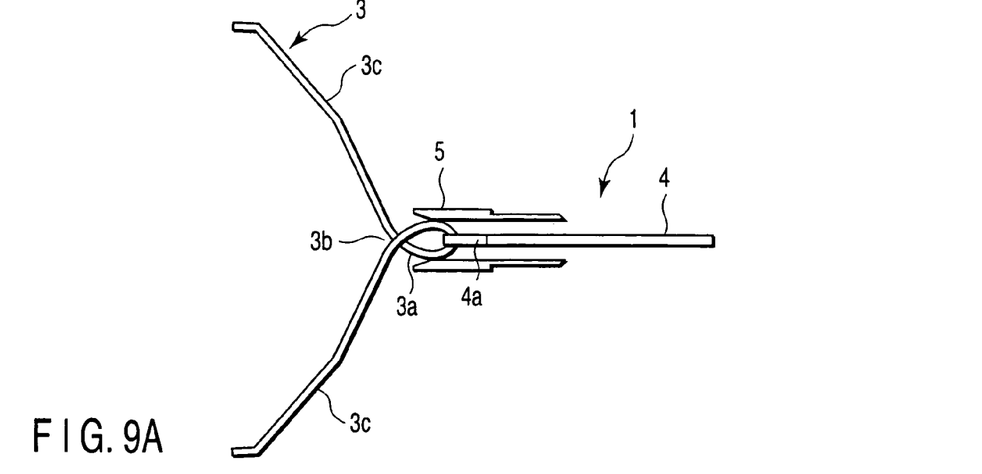
FIG. 9A is a longitudinal sectional view showing the state a base ring of a clip is inserted into a holder tube and the clip hands of the clip are expanded to a maximum expanded position in a clipping operation by a clip device.
Figure 9B:
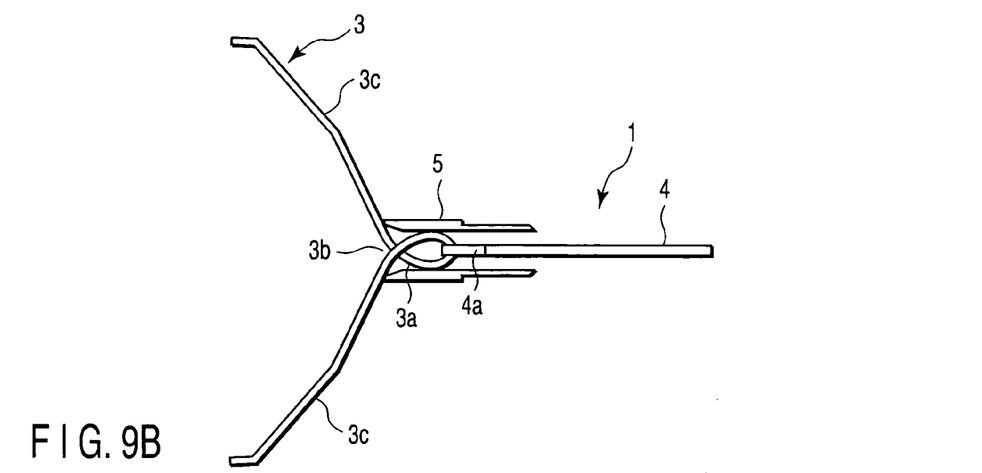
FIG. 9B is a longitudinal sectional view showing the state the clip hands of a clip expanded to a maximum expanded position contacts a holder tube.

(2) Pull the slider unit 15 a little toward the base end side, and extend the connection member 4 toward hand. By this operation, the base ring 3a is gradually pressed to fit into the holder tube 5, as shown in FIG. 9A. In this time, the base ring 3a pressed to fit into the holder tube 5 is gradually crushed, and deformed to have a smaller size (the diameter is reduced). At the same time, the clip hands 3c are deformed in the expanding direction, interlocking with the deformation of the base ring 3a, and expanded to the substantially maximum expanded position. While being held in the substantially maximum expanded state, the base ring 3a is completely inserted into the holder tube 5, as shown in FIG. 9B. In this state, let the clip 3 grip an object living tissue by the clip hands 3c.

(3) Then, pull the slider unit 15 further toward the base end side. By this operation, the connection member 4 is extended to the side close to hand, and the base of the clip hands 3c is pressed to fit into the holder tube 5. By the extension of the connection member 4 in this time, the clip hands 3c are moved in the closing direction to clip the living tissue by the clip hands 3c, as shown in FIG. 9C.

Figure 9C:
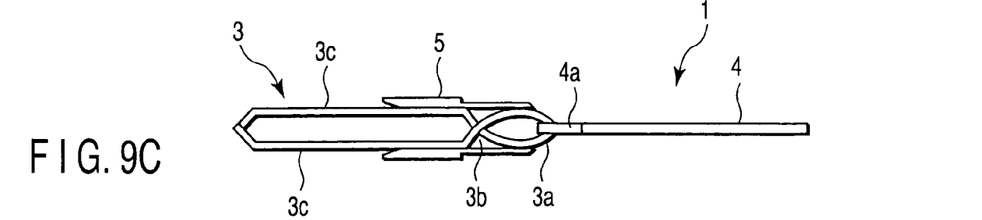
FIG. 9C is a longitudinal sectional view of an important part showing the state the clip hands of a clip are moved to a closed position.
Figure 9D:
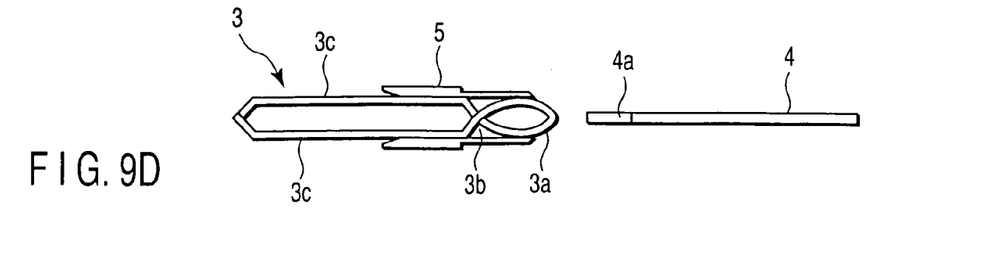
FIG. 9D is a longitudinal sectional view of an important part showing the state the hook of a connection plate is extended and a clip is disengaged from a base ring.
Figure 10A:
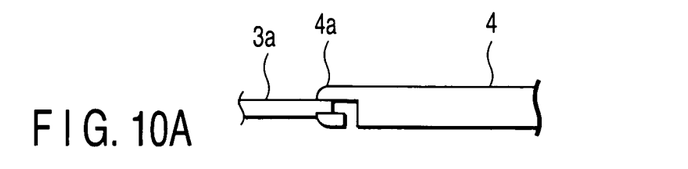
FIG. 10A is a side view of an important part showing the state the hook of a connection member is engaged with a base ring.
Figure 10B:
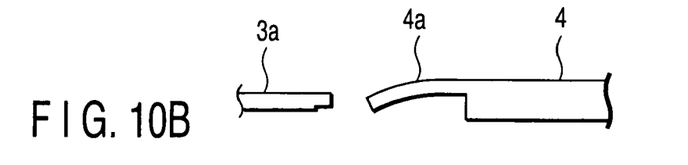
FIG. 10B is a side view of an important part showing the state the hook of a connection plate is extended and a clip is disengaged from a base ring.

Further, while the clip hands 3c are being closed as shown in FIG. 9C, pull the connection member 4 further to the side close to hand. By this operation, the substantially J-shaped hook 4a at the front end of the connection member 4 engaged with the base ring 3a is plastically deformed to the extended state, as shown in FIG. 10B. As a result, the base ring 3a and connection member 4 are disengaged, and the connection member 4 is separated from the base ring 3a. By this operation, the clip 3 is closed in being held by the holder tube 5, as shown in FIG. 9D.

Figure 11:
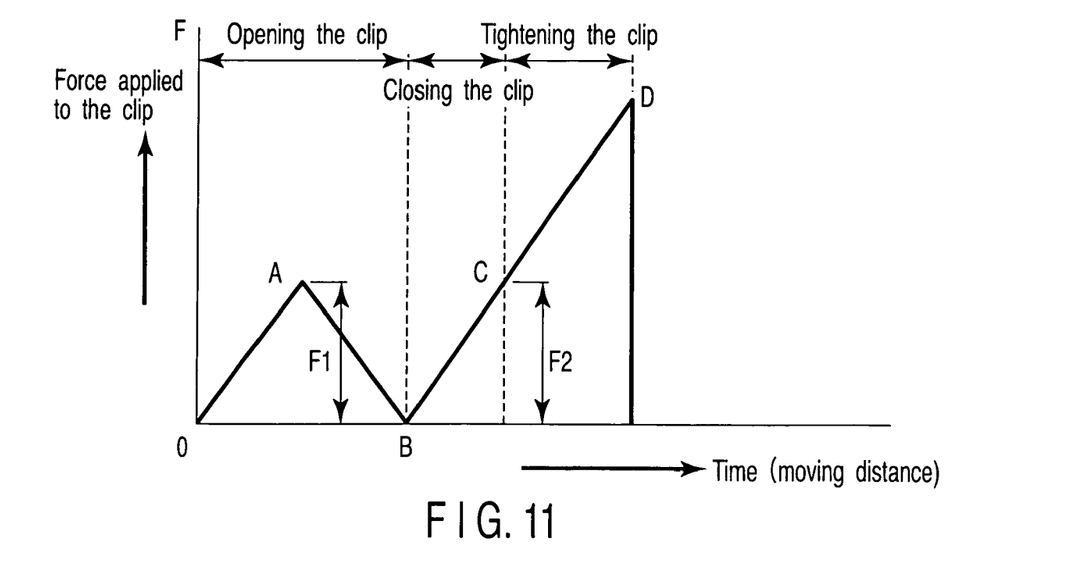
FIG. 11 is a characteristic diagram showing the relationship between the moving distance of a clip and the force applied to a clip in the clipping operation by a clip device.

FIG. 11 is a graph showing the changes in the force applied to the clip 3, when the slider unit 15 of the control unit 9 is pulled to the side close to hand when closing the clip 3. In FIG. 11, the point 0 indicates start of pulling the connection member 4, the point A indicates the time the base ring 3a is pressed to fit into the holder tube 5 as shown in FIG. 9A, the point B indicates the time the clip hands 3c of the opened clip 3 contact the holder tube 5 as shown in FIG. 9B, and the point C indicates the time the front ends of the clip hands 3c of the clip 3 contact each other and the clip hands close completely as shown in FIG. 9C. At the point A between 0 and B, the force of expanding the clip hands 3c becomes the maximum (force F1). In this time, the clip hands 3c are expanded to the substantially maximum expanded position. And, in the area between the points A and B, the clip hands 3c are held in the state expanded substantially maximum.

Further, in the states after the point B in FIG. 11, the clip hands 3c are moved in the closing direction by the extension of the connection member 4, and changed from the substantially maximum expanded state as shown in FIG. 9B, to the completely closed state as shown in FIG. 9C. At the point C, the force of closing the clip hands 3c is F2. In the state after the point C, the substantially J-shaped hook 4a at the front end of the connection member 4 engaged with the base ring 3a as shown in FIG. 10A, is switched to be plastically deformed to the extended state as shown in FIG. 10B. The point D indicates the time the engagement of the base ring 3a and connection member 4 is released, and the connection member 4 is separate from the base 3a, as shown in FIG. 10B.

When closing the clip unit 1 of the clip device configured as described above, pull the slider unit 15 of the control unit 9 toward the side close to hand, and pull the connection member 4. Then, expansions of the clip hands, clipping operation and disengaging operation succeed. To expand the clip hands, press the base ring 3a to fit into the holder tube 5, and expand the clip hands 3c. For the clipping operation, press the base of the clip hands 3c to fit into the holder tube 5, move the clip hands 3c in the closing direction, and let the clip hands 3c clip a living tissue. For the disengaging operation, deform plastically the substantially J-shaped hook 4a at the front end of the connection member engaged with the base ring 3a to the state of extending the hook 4a, and disengage the base ring 3a from connection member 4.

BRIEF SUMMARY OF THE INVENTION

According to the present invention, there is provided a clip device for holding a living tissue, included a clip having a base portion and a pair of clip hands extending from the base portion, the base portion being bent almost at a center, a holder tube arranged at a proximal portion of the base portion, for tightening a clip with a smaller diameter than the base portion, and a hold member filled in the holder tube. A clip hand expanding operation to expand the clip hands is performed by press fitting the base portion into the holder tube, and a clipping operation to let the clip hands hold a living tissue is performed closing the clip hands by press fitting the base of the clip hands into the holder tube. A force adjustment portion which adjusts the force of the clipping operation in the state of relatively increasing a ratio of a clip closing force to close the clip hands to a clip opening force to expand the clip hands.

Preferably, the force adjustment portion is provided with the hold member placed in the rear end side in the holder tube.

Preferably, the hold member is placed at the position contacting the base portion, in the state that the base portion is pressed to fit into the holder tube, and the clip hands are expanded to the maximum expanded position.

Preferably, the hold member has a solid part placed in the rear end side in the holder tube, and a hollow part placed in the front end side ahead of the solid part.

Preferably, the hold member has a first hold member with high hardness, and a second hold member with lower hardness than the first hold member, and the force adjustment means is provided with the second hold member placed in the front end side in the holder tube, and the first hold member placed in the rear end side in the holder tube.

Preferably, the force adjustment portion is provided with the hold member placed only in the front end side in the holder tube.

Further, preferably, the hold member is placed in a range of 50% of the total length of the holder tube from the front end face of the holder tube.

Further, preferably, the holder tube has a tapered surface in the inner circumference surface at the front end, and the hold member is placed only on the tapered surface of the holder tube.

Preferably, the hold member is mode of soft flexible material.

Preferably, the hardness of the flexible material is 40 degree or lower.

According to the present invention, there is provided a clip device for holding a living tissue, included a clip having a ring-like base portion made by bending at almost the center of a belt-like clip member, and a pair of clip hands extended almost straight from the base portion crossing each other, the clip having a characteristic of expanding the clip hands in the separating direction, a connection member having a front end and a base end, and is formed with an engagement part at the front end to engage with the base ring, a holder tube which is fit around the connection member, for tightening a clip with a smaller diameter than the base portion, and a hold member which is filled in the holder tube, and holds the connected portion of the base portion and connection member. A clip hand expanding operation to expand the clip hands is performed by press fitting the base portion into the holder tube by pulling the connection member to the side close to hand, and a clipping operation to let the clip hands hold the living tissue is performed by pulling the connection member in the direction of closing the clip hands by press fitting the base of the clip hands into the holder tube. A force adjustment portion which adjusts the force of the clipping operation in the state of relatively increasing a ratio of a clip closing force to close the clip hands to a clip opening force to expand the clip hands.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the embodiments given below, serve to explain the principles of the invention.

DETAILED DESCRIPTION OF THE INVENTION

Figure 1:
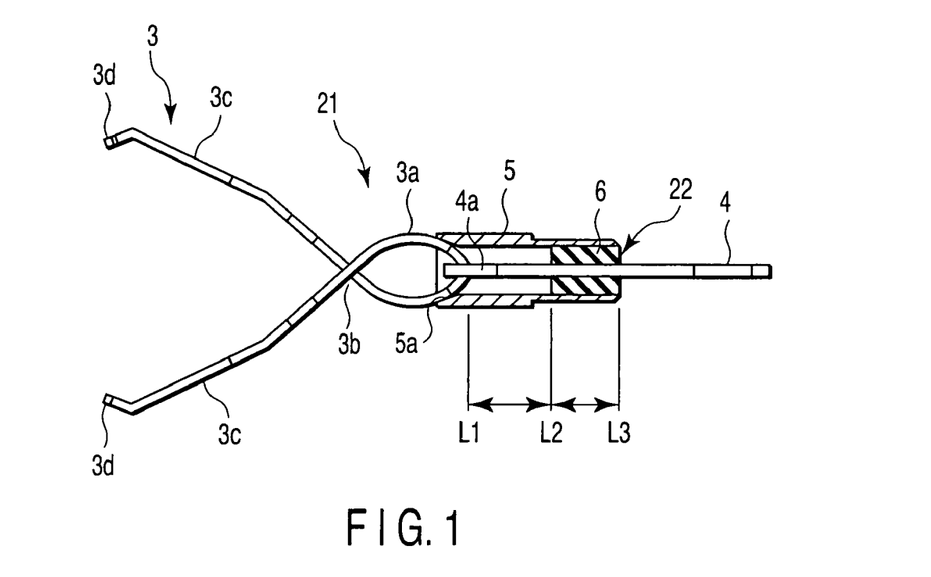
FIG. 1 is a longitudinal sectional view showing a clip unit of a living tissue clip device according to a first embodiment of the present invention.

Hereinafter, a first embodiment of the present invention will be explained with reference to FIG. 1 and FIG. 9 to FIG. 11. FIG. 1 shows a clip unit 21 of a living tissue clip device of this embodiment of the present invention. Most of the configuration of the clip unit 21 of this embodiment is the same as those of a clip unit 1 of FIGS. 8A–8D. Thus, in FIG. 1, the same reference numerals are given to the same parts as those in FIGS. 8A–8D, and detailed description will be omitted and only the different parts will be explained.

Namely, the clip unit 21 of this embodiment is provided with an operating force adjustment portion 22. In the clip operating force adjustment portion 22, the hold member 6 is placed in the rear end side (between L2 and L3) in the holder tube 5, as shown in FIG. 1. Thus, the resisting effect by the hold member 6 is reduced in the clip opening operation area to expand the clip hands 3c of the clip 3 (in the range between the points 0 and B in FIG. 11) when operating a clip. Further, the resisting effect by the hold member 6 is increased to larger than in the clip opening operation area, in the clip closing operation area to close the clip hands 3c (in the range between the points B and C in FIG. 11).

Further, the clip unit 21 of this embodiment has a tapered surface 5a in the inner circumference surface of the front end of the holder tube 5 whose inside diameter increases toward the front end. In the state the clip unit 21 is not closed, the base end part of the base ring 3a of the clip 3 is held in being contacted to the tapered surface 5a. Further, an inwardly curved claw 3d is formed at the front end of each clip hands 3c of the clip 3.

Now, explanation will be given on the function of this embodiment configured as described above. When closing the clip unit 1 for clipping, pull the slider unit 15 in the control unit 9 of the clip control unit 2, as explained above. Then, the connection member 4 is pulled toward the side close to hand, and the base ring 3a is gradually pressed to fit into the holder tube 5, as shown in FIG. 9A. In this time, the base ring 3a pressed and fit into the holder tube 5 is gradually crushed and deformed to have a smaller size (the diameter is reduced). At the same time, the clip hand 3c is deformed in the expanding direction, interlocking with the deformation of the base ring 3a. In this case, since the hold member 6 is not placed at the front end of the holder tube 5 (between L1 and L2 in FIG. 1) in this embodiment, the resisting effect by the hold member 6 is not applied to the clip opening force for clipping to expand the clip hands 3c, when expanding the clip hands 3c by gradually pressing the base ring 3a to fit into the holder tube 5. As a result, the clip hands 3c can be expanded to the substantially maximum expanded position by a relatively small force.

Further, in this embodiment, the hold member 6 is placed at the rear end of the holder tube 5 (between L2 and L3 in FIG. 1). Thus, the resisting effect by the hold member 6 can be applied to the clip closing force when closing the clip by closing the hold member 3c (from the time the clip hands 3c of the opened clip 3 contact the holder tube 5 (in FIG. 9B), to the time the front ends of the clip hands 3c of the clip 3 contact each other and the clip hands 3c are completely closed (in FIG. 9C)). As a result, the ratio of the clip closing force to close the clip hands 3c to the clip opening force to expand the clip hands 3c can be relatively increased.

The device configured as explained above provides the following effects. That is, in this embodiment, since the hold member 6 is placed in the rear end side in the holder tube 5, it is possible to decrease the resisting effect by the hold member 6 in the clip opening operation area to expand the clip hands 3c when operating a clip, and increase the resisting effect by the hold member 6 in the clip closing operation area to close the clip hands 3c to larger than that in the clip opening operation area. Thus, the difference of the operating force between the clip opening operation area and clip closing operation area can be increased while pressing the base ring to fit into the holder tube by pulling the connection member 4 toward the side close to hand. As a result, the time to switch from the clip opening operation area to the clip closing operation area can be confirmed by sense. Thus, it is easy to certainly stop the clip hands 3c by the operator's operation sense in the state expanded to the maximum expanded position when pulling the connection member 4 toward the side close to hand when operating a clip. Therefore, it is prevented that the connection member 4 is pulled toward the side close to hand exceeding the position where the clip hands 3c are expanded to the maximum expanded position when pulling the connection member 4 toward the side close to hand.

Figure 2:
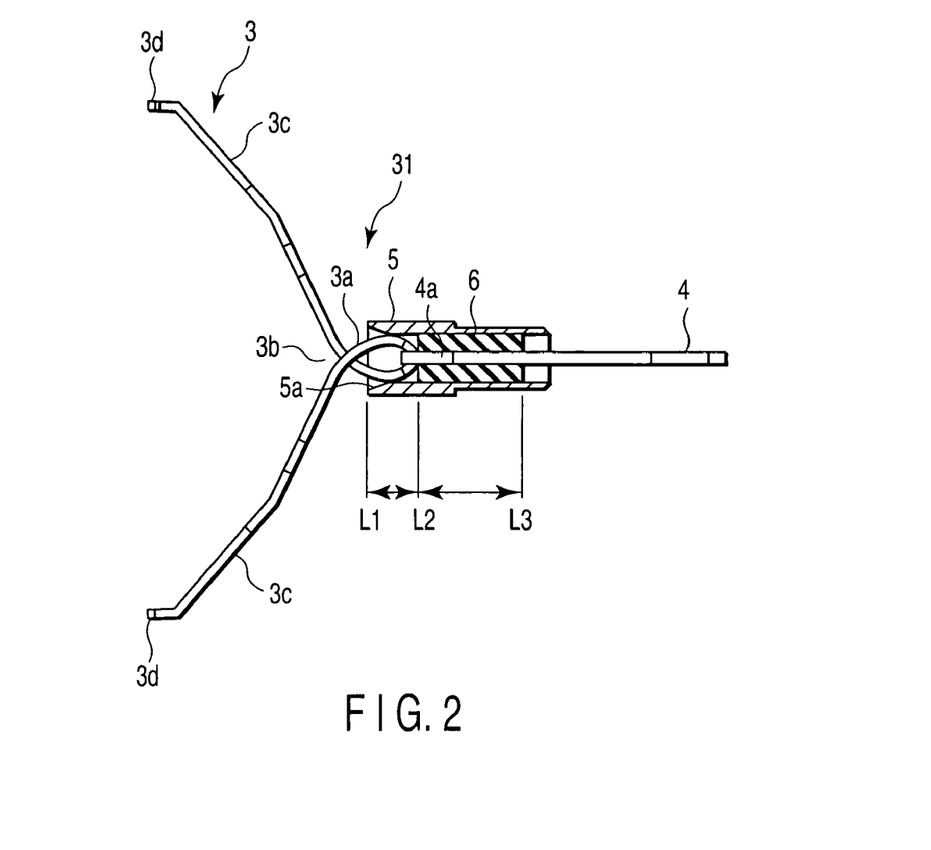
FIG. 2 is a longitudinal sectional view showing a clip unit of a living tissue clip device according to a second embodiment of the present invention.

FIG. 2 shows a second embodiment of the present invention. In the clip unit 31 of this embodiment, the front end position L2 of the hold member 6 placed in the rear end side in the holder tube 5 is extended forward. The front end position L2 of the hold member 6 is set at the position where the base ring 3a of the clip 3 contacts the hold member in the state the base ring 3a is pressed to fit into the holder tube 5 and the clip hands 3c are expanded to the maximum expanded position.

Now, the function of the above configuration will be explained. In the clip unit 31 of this embodiment, the base ring 3a does not contact the hold member 6 until the clip hands 3c reach the maximum expanded position in the clip opening operation area to expand the clip hands 3c when pulling the connection member 4 toward the side close to hand when operating a clip. Thus, it is possible not to apply the resisting effect by the hold member 6 to the resisting force to the operation of pulling the connection member 4 toward the side close to hand.

After the maximum expanded position, by contacting the base ring 3a to the hold member 6, it is possible to apply the resisting effect by the hold member 6 to the resisting force to the operation of pulling the connection member 4 toward the side close to hand.

In the above configuration, it is possible to decrease the resisting effect before the maximum expanded position in the clip opening operation area to expand the clip hands 3c when operating a clip, and increase the resisting effect after the maximum expanded position including the clip closing operation area to close the clip hands 3c. Thus, in this embodiment as in the first embodiment, it is possible to certainly stop the clip hands 3c at the maximum expanded position when pulling the connection member 4 toward the side close to hand when operating a clip, and increase ease of operating a clip.

Figure 3:
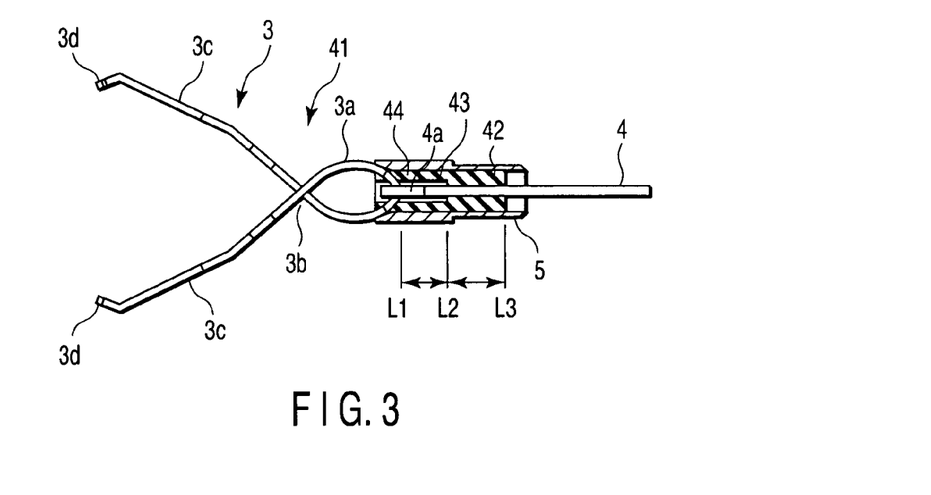
FIG. 3 is a longitudinal sectional view showing a clip unit of a living tissue clip device according to a third embodiment of the present invention.

FIG. 3 shows a third embodiment of the present invention. In a clip unit 41 of this embodiment, the configuration of the hold member 6 in the holder tube 5 is modified as described below. That is, in the hold member 6 of this embodiment, a solid part 42 is placed in the rear end side in the holder tube 5. And, a cylindrical part 44 formed with a hollow part 43 at the axial center is placed nearer to the front end than the solid part 42.

Now, explanation will be given on the function of this embodiment configured as described above. In the clip unit 41 of this embodiment, the base ring 3a contacts the cylindrical part 44 of the hold member 6 in the holder tube 5 in the clip opening operation area to expand the clip hands 3c when pulling the connection member 4 toward the side close to hand when operating a clip. Thus, it is possible to decrease the resisting effect by the hold member 6 applied to the resisting force to the operation of pulling the connection member 4 toward the side close to hand.

In the closing operation area to close the clip hands 3c when operating a clip, the base ring 3a contacts the solid part 42 of the hold member 6 (at the position L2 in FIG. 3). Thus, after the position L2 where the base ring 3a contacts the solid part 42 of the hold member 6, the resisting effect by the hold member 6 applied to the resisting force to the operation of pulling the connection member 4 toward the side close to hand can be increased.

In the above configuration, it is possible to decrease the resisting effect in the clip opening operation area to expand the clip hands 3c when operating a clip, and increase the resisting effect in the clip closing operation area to close the clip hands 3c to larger than in the clip opening operation area. Thus, in this embodiment as in the first embodiment, it is possible to certainly stop the clip hands 3c at the maximum expanded position when pulling the connection member 4 toward the side close to hand when operating a clip, and increase ease of operating a clip.

Further, particularly in this embodiment, since the cylindrical part 44 of the hold member 6 is placed in the front end side in the holder tube 5, it is possible to hold the base end part of the base ring 3a of the clip 3 in the state being contacted to the cylindrical part 44, even while the clip unit 41 is not closed. Thus, the connected part of the base ring 3a and connection member 4 can be held by the cylindrical part 44 at the front end of the holder tube 5, and the clip unit 41 can be stably held.

Further, since the hold member 6 is placed in the front end side in the holder tube 5, the frictional resistance between the holder tube 5 and clip 3 increases through the hold member 6, in the state the clip unit 41 is closed. Thus, when clipping a living tissue, the clip 3 is hard to separate from the holder tube 5, and a living tissue can be held tightened.

Figure 4:
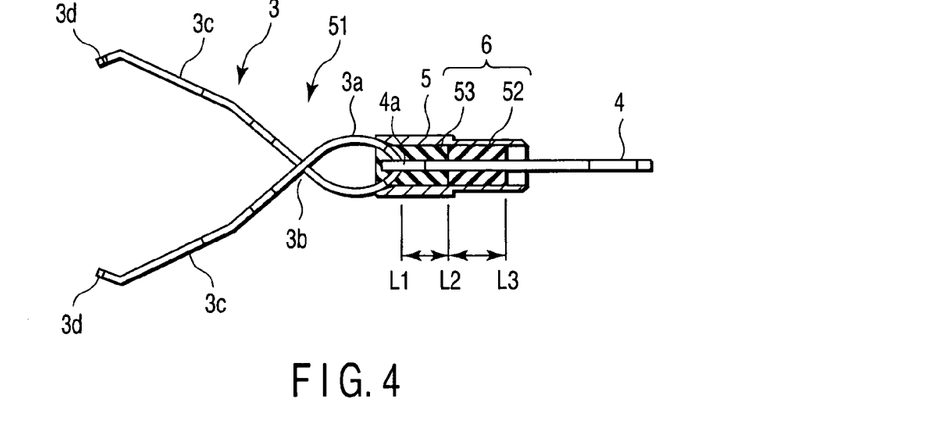
FIG. 4 is a longitudinal sectional view showing a clip unit of a living tissue clip device according to a fourth embodiment of the present invention.

FIG. 4 shows a fourth embodiment of the present invention. In a clip unit 51 of this embodiment, the configuration of the hold member 6 in the holder tube 5 is modified as described below. That is, the hold member 6 of this embodiment has a first hold member 52 with high hardness, and a second hold member 53 with lower hardness than the first hold member 52. The second hold member 53 is placed in the front end side in the holder tube 5, and the first hold member 52 is placed in the rear end side. The hardness of the first and second hold members 52 and 53 can be appropriately adjusted by changing an additive of a filling material such as silicone, or by changing the method of kneading the filling material such as silicone.

Now, the function of the above configuration will be explained. In the clip unit 51 of this embodiment, the base ring 3a contacts the low hardness soft hold member 53 placed in the front end side in the holder tube 5 in the clip opening operation area to expand the clip hands 3c when pulling the connection member 4 toward the side close to hand when operating a clip. Thus, it is possible to increase the resisting effect by the hold member 53 applied to the resisting force to the operation of pulling the connection member 4 toward the side close to hand.

In the clip closing operation area to close the clip hands 3c when operating a clip, the base ring 3a contacts the high hardness hold member 52 placed in the rear end side in the holder tube 5. Thus, thereafter, it is possible to increase the resisting effect by the hold member 52 applied to the resisting force to the operation of pulling the connection member 4 toward the side close to hand.

In the above configuration, it is possible to decrease the resisting effect in the clip opening operation area to expand the clip hands 3c when operating a clip, and increase the resisting effect in the clip closing operation area to close the clip hands 3c to larger than in the clip opening operation area. Thus, in the clip unit 51 of this embodiment as in the first embodiment, it is possible to certainly stop the clip hands 3c at the maximum expanded position when pulling the connection member 4 toward the side close to hand when operating a clip, and increase ease of operating a clip.

Further, in the clip unit 51 of this embodiment, the soft hold member 53 is placed in the front end side in the holder tube 5. Thus, it is possible to hold the base end part of the base ring 3a of the clip 3 in the state being contacted to the soft hold member 53, even while the clip unit 51 is not closed. Therefore, in the clip unit 51 of this embodiment, the connected part of the base ring 3a and connection member 4 can be held by the soft hold member 53 at the front end of the holder tube 5, and the clip unit 51 can be stably held, as in the third embodiment (refer to FIG. 3).

Further, since the hold member 53 is placed in the front end side in the holder tube 5, the frictional resistance between the holder tube 5 and clip 3 increases through the hold member 53 in the state. The clip unit 51 is closed. Thus, when clipping a living tissue, the clip 3 is hard to separate from the holder tube 5, and a living tissue is held tightened.

Figure 5:
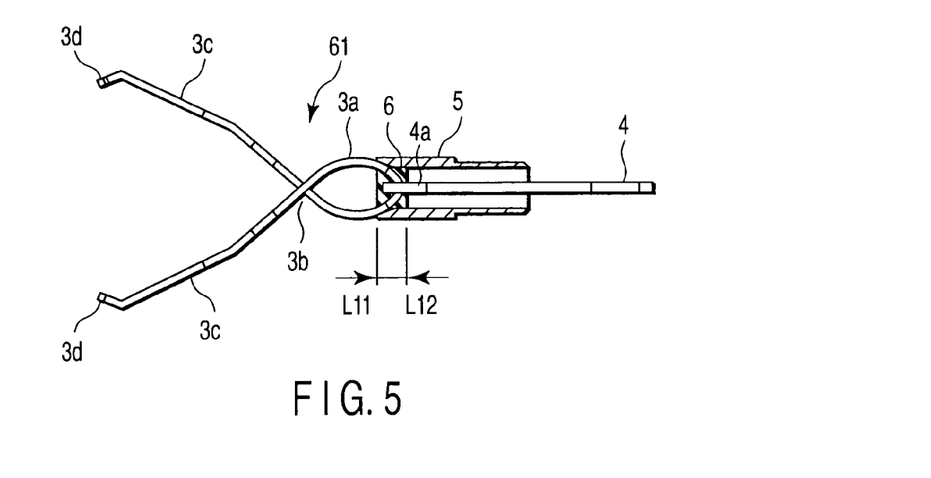
FIG. 5 is a longitudinal sectional view showing a clip unit of a living tissue clip device according to a fifth embodiment of the present invention.

FIG. S shows a fifth embodiment of the present invention. In a clip unit 61 of this embodiment, the hold member 6 is placed only in the front end side in the holder tube 5 (between L11 and L12). That is, the hold member 6 is placed in a range of 50% of the total length of the holder tube 5 from the front end surface of the holder tube 5, position L11, for example, in a range of 1–2 mm from the front end of the holder tube 5 whose total length is 4–5 mm.

Now, the function of the above configuration will be explained. In a clip unit 61 of this embodiment, the amount of the hold member 6 placed in the holder tube 5 can be decreased. Thus, it is possible to decrease the resisting effect by the hold member 6 occurred during the operation of pressing the base ring 3a to fit into the holder tube 5 by pulling the connection member 4 toward the side close to hand. Thus, only the operating force required to plastically deform the clip 3 when press fitting the base ring 3a when pulling the connection member 4 toward the side close to hand can be effected as a resisting force. Therefore, it is possible to increase the difference in the operating force between the clip opening operation area and clip closing operation area, while pressing the base ring 3a to fit into the holder tube 5 by pulling the connection member 4 toward the side close to hand.

In the above configuration, by the difference in the operating force between the clip opening operation area and clip closing operation area, it is possible to certainly stop the clip hands 3c by the operator's operation sense in the state expanded to the maximum expanded position when pulling the connection member 4 toward the side close to hand when operating a clip. Therefore, it is prevented that the connection member 4 is pulled toward the side close to hand exceeding the position where the clip hands 3c are expanded to the maximum expanded position when pulling the connection member 4 toward the side close to hand.

Further, particularly in the clip unit 61 of this embodiment, the hold member 6 is placed only in the front end side in the holder tube 5. Thus, it is possible to hold the base end part of the base ring 3a of the clip 3 in the state being contacted to the hold member 6, even while the clip unit 61 is not closed. Thus, the connected part of the base ring 3a and connection member 4 can be held by the hold member 6 at the front end of the holder tube 5, and the clip unit 61 can be stably held as in the third embodiment (refer to FIG. 3).

Further, since the hold member 6 is placed in the front end side in the holder tube 5, the frictional resistance between the holder tube 5 and clip 3 increases through the hold member 6 in the state the clip unit 61 is closed. Thus, when clipping a living tissue, the clip 3 is hard to separate from the holder tube 5, and a living tissue is held tightened.

Figures 6A, 6B:
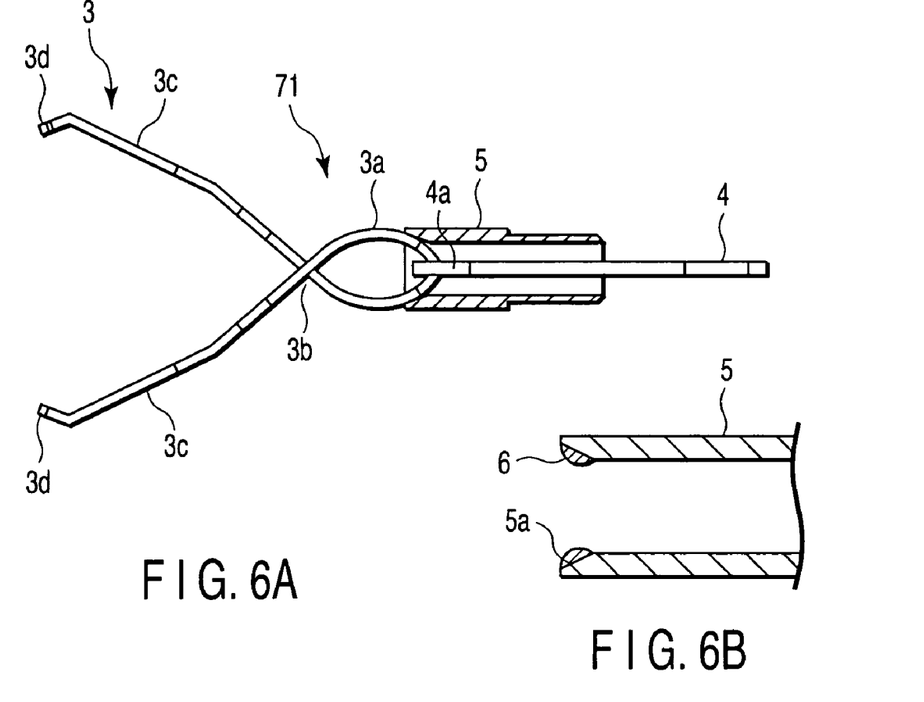
FIG. 6A is a longitudinal sectional view showing a clip unit of a living tissue clip device according to a sixth embodiment of the present invention.
FIG. 6B is a longitudinal sectional view showing a configuration of an important part of a clip unit.

FIGS. 6A and 6B show a sixth embodiment of the present invention. In a clip unit 71 of this embodiment, the hold member 6 is placed only in the tapered surface 5a of the holder tube 5, as shown in FIG. 6B.

In the clip unit 71 of this embodiment, the amount of the hold member 6 placed in the holder tube 5 can be further decreased. Thus, it is possible to further decrease the resisting effect by the hold member 6 occurred while pressing the base ring 3a to fit into the holder tube 5 by pulling the connection member 4 toward the side close to hand. Therefore, only the operating force required to plastically deform the clip 3 when press fitting the base ring 3a when pulling the connection member 4 toward the side close to hand, can be applied as a resisting force. As a result, it is possible to increase the difference in the operating force between the clip opening operation area and clip closing operation area, while pressing the base ring 3a to fit into the holder tube 5 by pulling the connection member 4 toward the side close to hand.

Therefore, in this embodiment as in the fifth embodiment (refer to FIG. 5), it is easy to certainly stop the clip hands 3c by the operator's operation sense in the state expanded to the maximum expanded position when pulling the connection member 4 toward the side close to hand when operating a clip. Therefore, it is prevented that the connection member 4 is pulled toward the side close to hand exceeding the position where the clip hands 3c are expanded to the maximum expanded position when pulling the connection member 4 toward the side close to hand.

Further, particularly in the clip unit 71 of this embodiment, since the hold member 6 is placed only in the tapered surface 5a in the holder tube 5, it is possible to hold the base end part of the base ring 3a of the clip 3 in the state being contacted to the hold member 6, even while the clip unit 71 is not closed. Thus, the connected part of the base ring 3a and connection member 4 can be held by the hold member 6 at the front end of the holder tube 5, and the clip unit 71 can be stably held as in the third embodiment (refer to FIG. 3).

Figure 7:
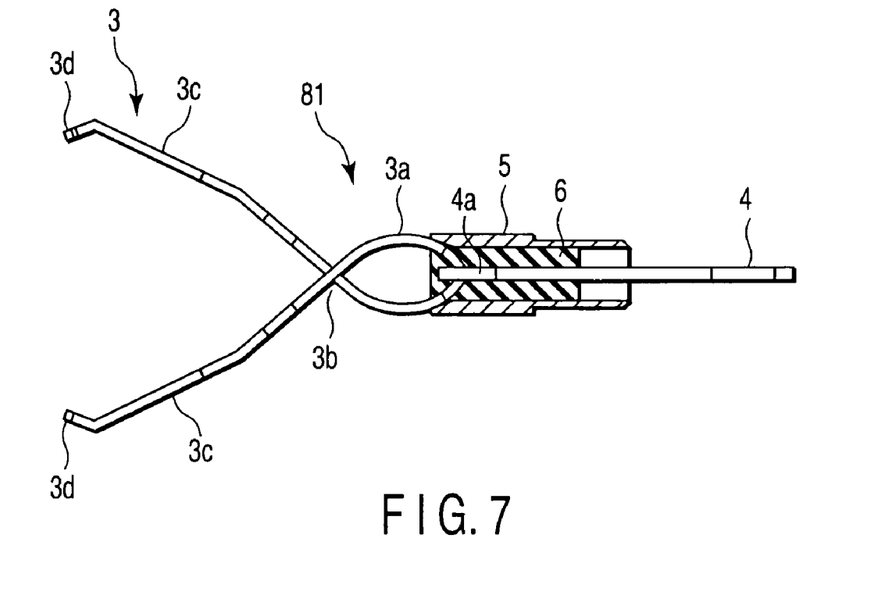
FIG. 7 is a longitudinal sectional view showing a clip unit of a living tissue clip device according to a seventh embodiment of the present invention.

FIG. 7 shows a seventh embodiment of the present invention. In a clip unit 81 of this embodiment, the hold member 6 is made of soft flexible material. For example, hardness of the soft flexible material of the hold member 6 is set to 40 degree or lower.

In the clip unit 81 of this embodiment, by placing the hold member 6 made of soft flexible material in the holder tube 5, it is possible to decrease the resisting effect by the hold member 6 occurred while pressing the base ring 3a to fit into the holder tube 5 by pulling the connection member 4 toward the side close to hand. Thus, by effecting only the operating force required to plastically deform the clip 3 when press fitting the base ring 3a when pulling the connection member 4 toward the side close to hand as a resisting force, the difference in the operating force between the clip opening operation area and clip closing operation area, while press fitting the base ring into the holder tube 5 by pulling the connection member 4 toward the side close to hand.

As a result, it is easy to certainly stop the clip hands 3c by the operator's operation sense in the state expanded to the maximum expanded position when pulling the connection member 4 toward the side close to hand when operating a clip. Therefore, it is prevented that the connection member 4 is pulled toward the side close to hand exceeding the position where the clip hands 3c are expanded to the maximum expanded position when pulling the connection member 4 toward the side close to hand.

Further, in the clip unit 81 of this embodiment, it is possible to hold the base end part of the base ring 3a of the clip 3 in the state being contacted to the hold member 6 even while the clip unit 81 is not closed. Thus, the connected part of the base ring 3a and connection member 4 can be held by the hold member 6, and the clip unit 81 can be stably held as in the third embodiment (refer to FIG. 3).

Further, since the hold member 6 is placed in the front end side in the holder tube 5, the frictional resistance between the holder tube 5 and clip 3 increases through the hold member 6 in the state the clip unit 81 is closed. Thus, when clipping a living tissue, the clip 3 is hard to separate from the holder tube 5, and a living tissue is held tightened.

The present invention is not to be limited by the above-mentioned embodiments. For example, though the hold member 6 is placed only in the tapered surface 5a of the holder tube 5 in the clip unit 71 of the sixth embodiment (refer to FIGS. 6A and 6B), it is also permitted to provide the hold member 6 in a thin film state all over the inner circumference surface of the holder tube 5, or to provide the hold member 6 in a part of the inner circumference surface of the holder tube 5.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A clip device for holding a living tissue, comprising:
    a clip having a base portion, and a pair of clip hands extending from the base portion, the base portion being bent almost at a center;
    a holder tube arranged at a proximal portion of the base portion, for tightening a clip with a smaller diameter than the base portion; and
    a hold member disposed in the holder tube;
    wherein a clip hand expanding operation to expand the clip hands is performed by press fitting the base portion into the holder tube, and a clipping operation to let the clip hands hold a living tissue is performed closing the clip hands by press fitting the base of the clip hands into the holder tube; and
    wherein the holder tube and the hold member comprise a force adjustment portion which adjusts a ratio of a clip closing force to close the clip hands to a clip opening force to expand the clip hands.

2. The clip device according to claim 1, wherein the hold member has a first hold member with high hardness, and a second hold member with lower hardness than the first hold member; and
    the force adjustment portion is provided with the second hold member placed in the front end side in the holder tube, and the first hold member placed in the rear end side in the holder tube.

3. The clip device according to claim 1, wherein the force adjustment portion is provided with the hold member placed only in the front end side in the holder tube.

4. The clip device according to claim 3, wherein the hold member is placed in a range of 50% of the total length of the holder tube from the front end face of the holder tube.

5. The clip device according to claim 4, wherein the holder tube has a tapered surface in the inner circumference surface at the front end; and
    the hold member is placed only on the tapered surface of the holder tube.

6. The clip device according to claim 1, wherein the hold member is made of soft flexible material.

7. The clip device according to claim 1, wherein the ratio of the clip closing force to the clip opening force is adjusted to be increased.

8. The clip device according to claim 7, wherein the force adjustment portion is provided with the hold member placed in the rear end side in the holder tube.

9. The clip device according to claim 8, wherein the hold member is placed at the position contacting the base portion, in the state that the base portion is pressed to fit into the holder tube, and the clip hands are expanded to the maximum expanded position.

10. The clip device according to claim 1, wherein the ratio of the clip closing force to the clip opening force is adjusted to be decreased.

11. The clip device according to claim 10, wherein the force adjustment portion is provided with the hold member placed in the rear end side in the holder tube.

12. The clip device according to claim 11, wherein the hold member is placed at the position contacting the base portion, in the state that the base portion is pressed to fit into the holder tube, and the clip hands are expanded to the maximum expanded position.

13. The clip device according to claim 10, wherein the hold member has a first hold member with high hardness, and a second hold member with lower hardness than the first hold member; and
    the force adjustment portion is provided with the second hold member placed in the front end side in the holder tube, and the first hold member placed in the rear end side in the holder tube.

14. The clip device according to claim 10, wherein the force adjustment portion is provided with the hold member placed only in the front end side in the holder tube.

15. The cup device according to claim 14, wherein the hold member is placed in a range of 50% of the total length of the holder tube from the front end face of the holder tube.

16. The clip device according to claim 15, wherein the holder tube has a tapered surface in the inner circumference surface at the front end; and
    the hold member is placed only on the tapered surface of the holder tube.

17. The clip device according to claim 10, wherein the hold member is made of soft flexible material.

18. A clip device for holding a living tissue, comprising:
    a clip having a ring-like base portion made by bending at almost center of a belt-like clip member, and a pair of clip hands extended almost straight from the base portion crossing each other at a point, the clip having a characteristic of expanding the clip hands in the separating direction;
    a connection member which has a front end and a base end, and is formed with an engagement part at the front end to engage with the base portion;
    a holder tube which is fit around the connection member, for tightening a clip with a smaller diameter than the base portion; and
    a hold member which is disposed in the holder tube, and holds a connected portion of the base portion and connection member;
    wherein a clip hand expanding operation to expand the clip hands is performed by press fitting the base portion into the holder tube by pulling the connection member to the side close to hand, and a clipping operation to let the clip hands hold a living tissue is performed by pulling the connection member in the direction of closing the clip hands by press fining the base of the clip hands into the holder tube; and
    wherein the holder tube and the hold member comprise a force adjustment portion which adjusts a ratio of a clip closing force to close the clip hands to a clip opening force to expand the clip hands.

* * * * *